Figure 1:
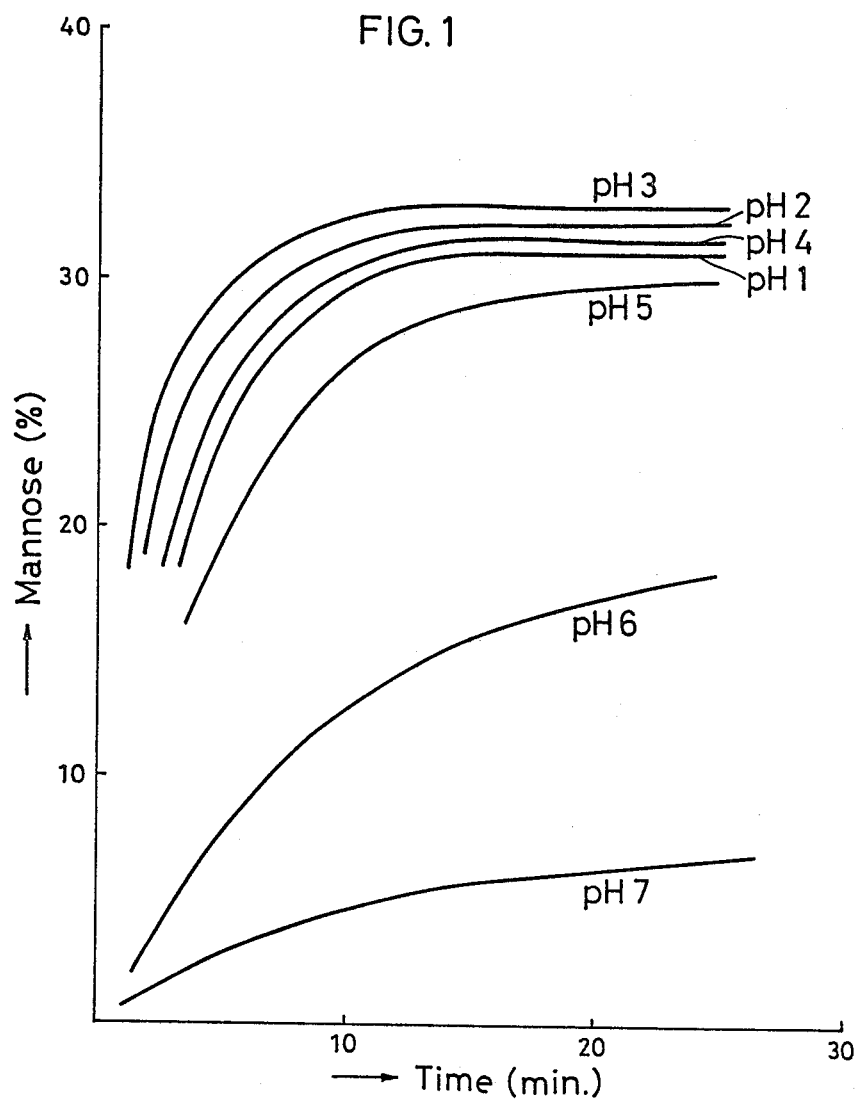

United States Patent [19]
Takemura et al.

[11] 4,083,881
[45] Apr. 11, 1978

[54] PROCESS FOR PREPARING D-MANNITOL

[75] Inventors: Motohiro Takemura, Soka; Mochihiro Iijima, Kuki; Yoshiaki Tateno, Misato; Yuji Osada, Tokyo; Hiroyuki Maruyama, Okegawa, all of Japan

[73] Assignee: Towa Kasei Kogyo Co., Ltd., Japan

[21] Appl. No.: 749,623

[22] Filed: Dec. 13, 1976

[30] Foreign Application Priority Data
Dec. 19, 1975  Japan .................. 50-150637

[51] Int. Cl.² .......................... C07C 29/00
[52] U.S. Cl. ................ 260/635 C; 195/31 R; 260/637 R; 536/1
[58] Field of Search .................. 260/635 C

[56] References Cited
U.S. PATENT DOCUMENTS

| | | | |
|---|---|---|---|
| 2,280,975 | 4/1942 | Power | 260/635 C |
| 2,642,462 | 6/1953 | Kasehagen | 260/635 C |
| 2,749,371 | 6/1956 | Kasehagen | 260/635 C |
| 3,329,729 | 7/1967 | Brandner et al. | 260/635 C |

OTHER PUBLICATIONS

B.L.K et al, "Angew. Chem." International edition in English, vol. 10, July–Dec. 1971, p. 909.

Primary Examiner—Joseph E. Evans
Attorney, Agent, or Firm—McGlew and Tuttle

[57] ABSTRACT

A D-glucose solution is added molybdic acid compound thereto and heated at a temperature of 110°–160° C with pH 2.0–4.5 to perform epimerizing reaction of D-glucose, and thereby 30–36%, based on the D-glucose, of D-mannose is formed. To the epimerized mixture thus obtained is further added glucose-isomerase to perform enzymatic isomerizing reaction of D-glucose remaining in the epimerized mixture, thereby 46% based on the remaining D-glucose is converted into D-fructose. The epimerized mixture or enzymatically isomerized mixture is subjected to catalytic hydrogenation under high pressure, and thereby is produced D-mannitol at high yield based on the initial D-glucose.

11 Claims, 2 Drawing Figures

PROCESS FOR PREPARING D-MANNITOL

BACKGROUND OF THE INVENTION

1. Field of the Invention

This invention relates to a process for preparing D-mannitol. More particularly, the invention relates to a process for preparing D-mannitol, which comprises isomerization(s) of D-glucose to convert a portion of the D-glucose into D-mannose alone or into D-mannose and D-fructose, followed by catalytic hydrogenation of the resulting mixture of sugars under high hydrogen pressure.

D-mannitol has recently come into wide use as the materials for medicines, foodstuffs and chemical products. Generally, D-mannitol occurs spontaneously in plant bodies, especially in marine plants. D-mannitol is also formed chemically through hydrogenation of D-mannose or D-fructose. The theoretical formation ratio of D-mannitol from D-mannose through the hydrogenation is 100%, while that of D-mannitol from D-fructose is 50% because of half mole of D-fructose used being transformed to D-sorbitol. (In this specification and claims, both "%" and "part" are on the dried matter basis).

2. The Prior Art

D-mannitol is currently prepared chemically in such a manner as 100 part sucrose is inverted (i.e., hydrolyzed) to form a mixture of 52 part D-glucose and 52 part D-fructose and the mixture is hydrogenated to transform it to a mixture of D-sorbitol and D-mannitol followed by crystallization of D-mannitol to separate therefrom. However, according to this process, formation ratio of D-fructose from the sucrose used is 52% at most, so that that of D-mannitol by the hydrogenation reduces, from the above-mentioned theoretical formation ratio (i.e., 50%) of D-mannitol from D-fructose, necessarily to 26% or below, resulting in the yield of crystalline D-mannitol being about 17% based on the initial material, because of a considerable amount of D-mannitol remaining inevitably in the mother liquor at the crystallizing step.

In connection with the above, it is known that D-glucose is isomerized to convert a portion of it into D-fructose and/or D-mannose in the presence of an enzyme or base. The chemical formula of such isomerization of D-glucose is represented as below. (Among these isomerizing reactions of sugars, such ones as the conversion of D-glucose into D-mannose are specifically or restrictedly defined as epimerization.)

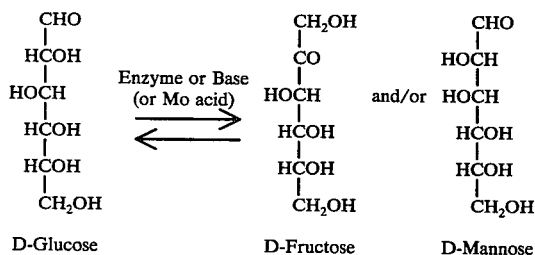

Known examples of the isomerization of D-glucose are as follows: When glucose-isomerase is added to an aqueous solution of 100 part D-glucose and the resultant mixture is warmed at a temperature of 65° C for 3 days, there is formed an equilibrium mixture of 54 part D-glucose and 46 part D-fructose. There is further, when a saturated lime solution containing 100 part D-glucose is held at a temperature of 35° C for 5 days, formed an equilibrium mixture of 63.5 part D-glucose, 31.0 part fructose, 2.5 part D-mannose and 3.0 part impurities. As for the latter process, rise in the reaction temperature results in lowering of the formation ratio of D-fructose.

Furthermore, it has been disclosed lately in Angew. Chem., 83(23), 967 (1971) as well as specification of Czechoslovakian patent No. 149,051 that an equilibrium mixture of 75 part D-glucose and 25 part D-mannose is obtained without any formation of D-fructose, when 1 part molybdic acid is added to an aqueous solution of low concentration (i.e., about 17%) of 100 part D-glucose and the resultant mixture is heated at a temperature of 70°–100° C for 5–10 hours with pH 7.0 or below (any adjustment of pH values of the reaction systems is not however conducted in the examples of these literatures, while about pH 5 has been exhibited by the trace-experiments of such examples carried out by us).

However, the equilibrium mixture(s) of D-glucose, D-fructose and/or D-mannose obtained by the isomerizations or epimerization, of D-glucose, as mentioned above, are all, from the content(s) of D-fructose and/or D-mannose thereof, expected to be, when submitted to the preparation of D-mannitol, only equivalent to or below the said mixture of 52 part D-glucose and 52 part D-fructose formed by the current chemical process, in point of the D-mannitol formation ratio therefrom based on the initial material.

SUMMARY OF THE INVENTION

We studied the isomerizing reaction of D-glucose, especially the epimerizing reaction of D-glucose according to the process of Czechoslovakian patent and have found that when this epimerization reaction is conducted under the conditions of a low pH and a high temperature, that is, of pH 2.0–4.5 and temperature of 110°–160° C, the D-mannose formation ratio based on the D-glucose used is improved remarkably (e.g., to the extent of 30–36%) beyond the critical composition ratio of D-glucose and D-mannose (75 : 25) obtained by the said conventional process. Under such our reaction conditions as above, the epimerization reaction can also be effected with D-glucose solution of high concentration and a little amount of molybdic acid compound. Furthermore, the reaction period thereof is very short, for instance, less than 40 minutes.

Thus, the mixture of D-glucose and D-mannose obtained in the above is subjected to the catalytic hydrogenation, thereby is formed D-mannitol at a high ratio such as 30–36% based on the initial D-glucose, which results in such a high yield of crystalline D-mannitol as 25–30%.

OBJECTS OF THE INVENTION

An object of the invention is accordingly to provide a process for preparing D-mannitol from D-glucose at high yield.

Another object of the invention is to provide a process for preparing D-mannitol from D-glucose with a simplified operation.

Still another object of the invention is to provide a process for preparing D-mannitol from D-glucose with a short time operation.

The other objects and advantages of the invention will be apparent from the detailed explanation of the invention described hereinafter.

DESCRIPTION OF THE INVENTION

Figure 2:
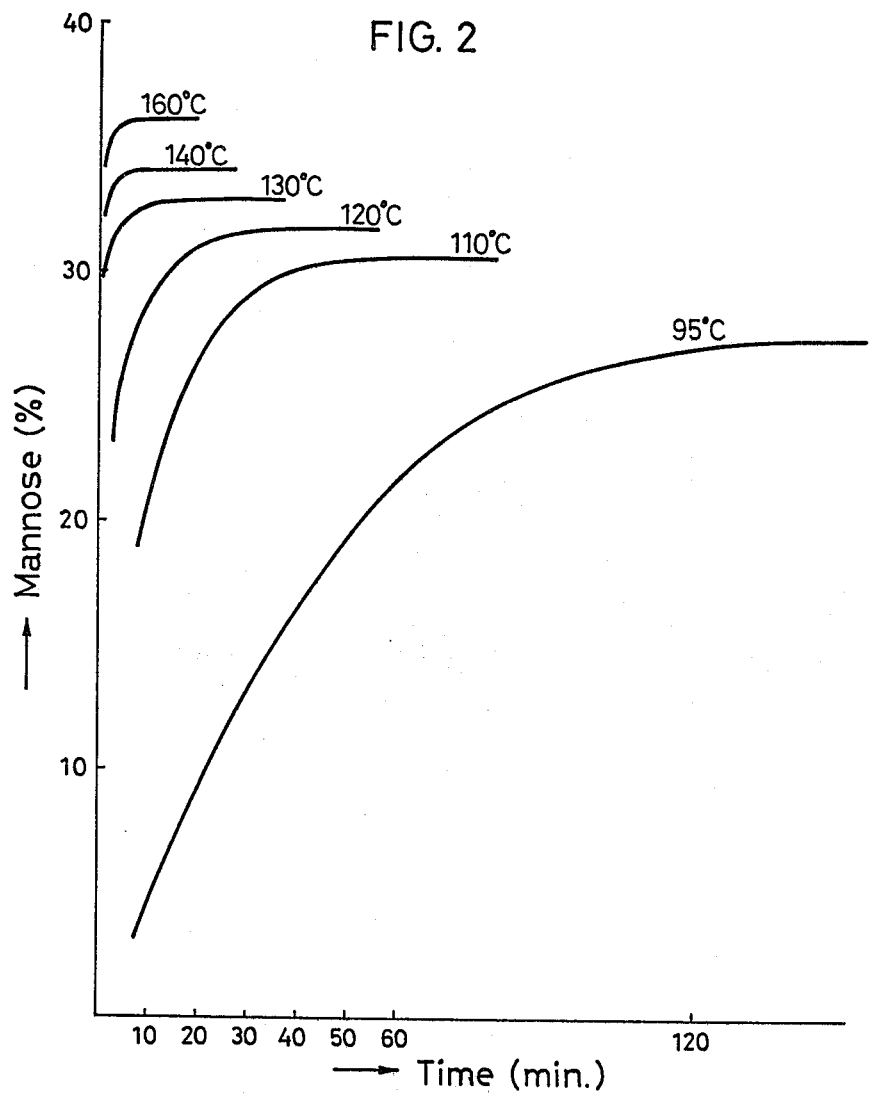

Referring now to the drawings, FIG. 1 is a graph illustrating the relationship between the D-mannose formation ratio based on the D-glucose used and the reaction period, when to a 60% D-glucose aqueous solution is added ammonium molybdate in an amount of 0.2% based on the D-glucose and the resulting mixture is heated at a temperature of 130° C, but with pH value varying from 1 to 7, and FIG. 2 is a graph similarly illustrating the relationship of D-mannose formation ratio-reaction period, when the mixture of 60% D-glucose aqueous solution and 0.2% of ammonium molybdate as above is adjusted to pH 3.0 with dilute sulfuric acid and heated at a reaction temperature varying from 95° C to 160° C.

According to the first step (i.e., epimerizing reaction of D-glucose) of the process of the present invention, a mixture of a D-glucose aqueous solution and molybdic acid compound is adjusted to pH 2.0–4.5, preferably to 3.0–4.0, and heated at a temperature of 110°–160° C, thereby the reaction is performed within a short time, e.g., about 40 minutes, at high formation ratio of D-mannose based on the D-glucose material used. The reaction is further performed effectively even when a high concentration solution of D-glucose (e.g., 40–80%) and a little amount of molybdic acid compound are employed.

Epimerization reaction of the present process as above will be probably promoted by the effect of co-operation (or synergism) of pH with temperature, of the reaction system, to give high formation ratio of D-mannose. With rise in the reaction temperature in the range of 110°–160° C, the formation ratio of D-mannose increases and the reaction period is shortened, proportionally thereto. In FIG. 2, for instance, the formation ratio of D-mannose amounts to about 32% in about 30 minutes at a reaction temperature of 120° C; to about 34% in about 7 minutes at 140° C; and to about 36% in about 4 minutes at 160° C, respectively. However, in case the temperature exceeds 160° C, the reaction system becomes deep in color by decomposition of the sugars contained therein.

The required time for the epimerization reaction of the present process is so markedly shortened that the application of a continuous reaction system is readily attained to this reaction. For instance, a D-glucose solution added molybdic acid compound thereto is pumped continuously under pressure into a reaction pipe having a predetermined length from an end of the pipe and heated under pressure while it flows through the reaction pipe, thereby the finished solution is discharged continuously from the other end of the pipe.

Values of pH of the epimerization reaction system of the present process also affect the formation of D-mannose remarkably, as can be seen from FIG. 1. When pH value exceeds 4.5 there appears lowering of the D-mannose formation ratio, while with pH below 2.0 it is observed that the solution becomes deep in color by decomposition of sugars. In order to adjust pH value of the reaction system, is used either inorganic acid such as hydrochloric acid, sulfuric acid or phosphoric acid, or organic acid such as oxalic acid.

According to the process of epimerizing reaction of D-glucose described in specification of said Czechoslovakian patent, the reaction system was, as mentioned previously, heated at a temperature below 100° C for 5–10 hours, presumably with pH 5–7. Therefore, it will be understood that combination of the conditions of the epimerization reaction of the present process, that is, the combination of low pH of 2.0–4.5, high reaction temperature of 110°–160° C and short reaction period such as 4–40 minutes constitutes a novel feature that has never been known.

Molybdic acid compound used for the epimerization reaction of this process includes ammonium molybdate, sodium molybdate, potassium molybdate, molybdenum trioxide, molybdic acid, and the like. With increase in the amount of molybdic acid compound to be added, the reaction velocity becomes larger while the D-glucose material is more decomposed by side-reactions. Favourable amount of the molybdic acid compound used for the epimerization reaction of the present process is however only 0.05–0.20% relative to the initial D-glucose which corresponds to about 1/20 to 1/5 the amount of molybdic acid used for the conventional process. (In case of using however such D-glucose material containing much impurities as hydrol described hereinafter, the amount (%) of molybdic acid compound is calculated on the overall dried matter of the D-glucose material). Such a reduction of the amount of molybdic acid compound (i.e., catalyst) depends exclusively on the great difference between the conditions of the epimerization reaction of the present process and those of the conventional process. Reduction of the amount of the catalyst used is also advantageous in that the refining treatment thereafter becomes more facile.

The D-glucose material for the epimerization reaction of the present process, includes crystalline D-glucose, starch hydrolyzate, so-called hydrol which is the concentrate of starch hydrolyzate from which crystalline D-glucose has been separated, and the like. As to an impure material of D-glucose such as hydrol, it is preferable to use that Dextrose Equivalent (hereinafter abridged to DE) of which is above 80.

Finished solution of the epimerization reaction (or epimerized mixture) thus obtained is yellow or light brown in color and contains, for instance, 30–36%, relative to the D-glucose used, of D-mannose. The epimerized mixture is, for example, decolorized with a little amount of active carbon, and further refined by ion exchange resin treatment to give a colorless and transparent solution. This refined solution exhibits pH 5.0–7.0.

According to the second step of the process of the present invention, the epimerized mixture or its refined solution is subjected to the catalytic hydrogenation reaction under high pressure. For example, the refined solution is adjusted to have 50–70% dried matter, added thereto a hydrogenating catalyst such as nickel catalyst (e.g., Raney nickel) or platinum group catalyst (e.g., platinum, ruthenium or palladium) and heated, while agitated, at a temperature of 110°–160° C for 1.0–2.5 hours under a hydrogen pressure of 100–200 kg./cm$^2$. Dried matter composition of the finished solution of the hydrogenating reaction (or hydrogenated mixture) thus obtained is, when crystalline D-glucose have been employed as the material for the epimerization reaction, for instance, 70–64% D-sorbitol and 30–36% D-mannitol. When the epimerized mixture which is not refined undergoes the catalytic hydrogenation, the amount of the hydrogenating catalyst to be used is increased a little, thereby is obtained the D-mannitol formation ratio almost similar to that obtained by the epimerized mixture having been refined.

The hydrogenated mixture is, for example, filtered to remove the catalyst, decolorized with active carbon, treated with ion exchange resins, and concentrated in vacuo followed by cooling to crystallize out D-mannitol. The yield of crystalline D-mannitol amounts, for instance, to 25–30% based on the initial D-glucose, which yield is superior greatly to that by the conventional process, that is, about 17%.

Furthermore, when such an impure D-glucose material as hydrol containing oligosaccharides is used for the epimerization reaction of the present process, the subsequent (or later) hydrogenation reaction is advantageously effected by employing the reaction conditions of low pH such as 2–3 and high temperature such as 160°–180° C, thereby hydrogenation involving hydrolyzation, of the oligosaccharides, occurs so that the viscosity of the hydrogenated mixture formed lowers resulting in improvement in the yield of crystalline D-mannitol.

Next, we further studied the possibility of enzymatic isomerization of the D-glucose which coexists with D-mannose in the epimerized mixture of the present process having been described above. We have firstly tested whether the isomerizing reaction to be caused by glucose-isomerase is not inhibited by the molybdic acid compound which has remained inevitably in the epimerized mixture. We have further tested the influence of the glucose-isomerase added thereto on the equilibrium formed between D-glucose and D-mannose in the epimerized mixture.

As the result of the above studies, we have found that such enzymatic isomerization is, when the amount of the molybdic acid compound in the epimerized mixture has been below 0.4% relative to the dried matter of this mixture, effected normally so as to about 46%, at its maximum, based on the D-glucose remaining in the epimerized mixture be converted into D-fructose without being influenced by the coexisting D-mannose. To the contrary, in case the amount of the molybdic acid compound exceeds 0.4%, there appears reduction of the D-fructose formation ratio and extension of the period, of the isomerization reaction. Therefore, in other words, the enzymatic isomerization reaction of the present process can be conducted effectively by employing the epimerized mixture without any refining treatment of it but adjustment of pH, when the amount of molybdic acid compound in the epimerized mixture has been below 0.4%. This results in an advantage of the present process that the operation is simplified significantly.

The enzymatic isomerization reaction of the present process is, for instance, carried out in such a manner as the epimerized mixture is adjusted to pH 6.5–8.5 and to have 50–65% dried matter and added a predetermined amount of glucose-isomerase thereto followed by warming the resultant aqueous mixture at a temperature of 65°–75° C for 48–72 hours, while agitated gently and maintained at pH 6.5–8.5. Finished solution of the isomerization reaction (or isomerized mixture) is, for example, filtered to separate the enzyme, treated with active carbon and further with ion exchange resins to give a colorless, transparent solution. Refined solution obtained exhibits pH 5.0–7.0 and its dried matter composition is, when crystalline D-glucose have been employed as the material for the initial epimerization reaction, for instance, 39–35% D-glucose, 31–29% D-fructose and 30–36% D-mannose.

Isomerization reaction of the present process may also be conducted by using the so-called immobilized enzyme system. For instance, glucose-isomerase is adsorbed to a suitable carrier, with which is filled a column having a predetermined length, and the epimerized mixture is made to flow continuously through the column at a suitable rate, thereby the remaining D-glucose in the epimerized mixture is isomerized enzymatically while has been retained in the column.

To the glucose-isomerase to be used for the enzymatic isomerization reaction of the present process, are available all enzyme preparations of this kind being on the market, which have been prepared from the cultured materials of the microorganisms belonging to genus Streptomyces, Pseudomonos, Aerobacter, and the like. With increase in the amount of glucose-isomerase used, the reaction velocity of the isomerization becomes larger and the formation ratio of D-fructose is improved. For the industrial application however, it is preferable to use 0.5–2.0%, relative to the dried matter of the D-glucose material for the epimerization reaction, of an enzyme preparation having about 1,000 GIU/g. of enzyme activity, if 1 GIU is defined to represent such an enzyme activity that produces 1 mg. of D-fructose at a temperature of 70° C in 60 minutes.

The refined solution of the isomerized mixture can be subjected to the catalytic hydrogenation in the similar manner to that applied to the refined solution of the epimerized mixture described previously. For instance, the refined solution of the present isomerized mixture is adjusted to have about 50–70% dried matter, and heated, while agitated, under hydrogen pressure in the presence of a hydrogenating catalyst. Composition of the dried matter of the hydrogenated mixture thus obtained is, when crystalline D-glucose have been used as the material for the epimerization reaction, for instance, 54–50% D-sorbitol and 46–50% D-mannitol. On refining and concentrating the hydrogenated mixture, crystalline D-mannitol is obtained at such a high yield as 40–45% based on the initial D-glucose.

According to the process of the present invention, respective compositions of the epimerized mixture, the enzymatically isomerized mixture and the hydrogenated mixture, are determined quantitatively by means of gas liquid chromatography which has been recently applied widely to the separating estimation of components in a mixture of sugars and/or sugar alcohols. D-sorbitol and D-mannitol in the hydrogenated mixture of the present process are both estimated effectively after have been converted into hexaacetyl ester thereof. However, D-glucose and D-mannose in the epimerized mixture as well as D-glucose, D-mannose and D-fructose in the isomerized mixture are difficult to estimate separately, because the peaks either of them or of their derivatives on gas chromatograms have interfered with each other. Therefore, the compositions of such sugar mixtures are counted backward from the respective quantities of D-sorbitol and D-mannitol estimated by gas chromatography after these sugar mixtures having once been hydrogenated, applying the respective theoretical formation ratio(s) of D-sorbitol and/or D-mannitol from D-glucose, D-mannose or D-fructose mentioned previously.

Dried matter of the D-glucose materials containing much impurities, such as hydrol, refers to that having been dried in vacuo at a temperature of 95°–100° C for 16 hours.

A flowsheet of the reaction steps of the present invention using crystalline D-glucose as the material is illustrated as below:

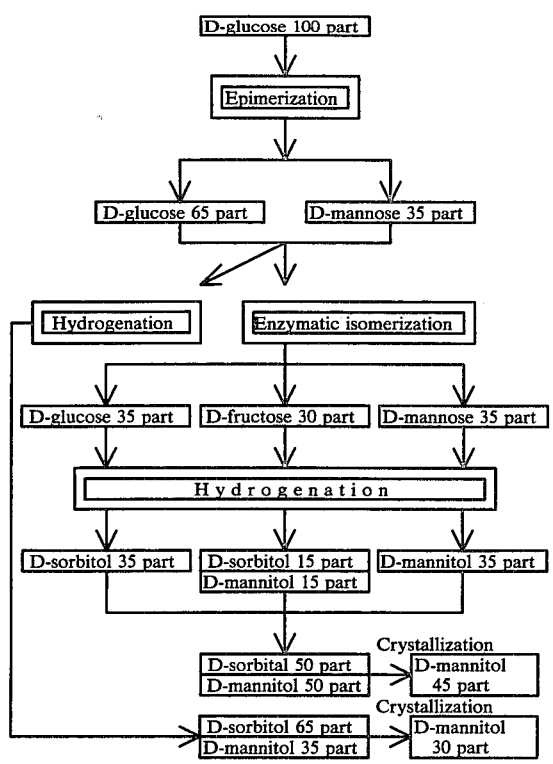

The following Examples serve to illustrate the invention without limiting it in any way:

EXAMPLE 1

3.3 kg. of crystalline D-glucose (with 9% crystal water content; hereinafter the same) being on the market is dissolved in 1.7 kg. of deionized water. The resulting solution is added thereto 6.0g. (corresponds to 0.20% relative to the D-glucose) of ammonium molybdate $(NH_4)_6 \cdot Mo_7O_{24} \cdot 4H_2O$, adjusted to pH 2.5 with a dilute sulfuric acid and heated in an autoclave of 10 liter-capacity, while agitated, at a temperature of 115° C for 40 minutes, to perform the epimerizing reaction of the D-glucose. Epimerized mixture obtained exhibits pH 2.2 and is light yellow in color. After cooled, this mixture is decolorized with a little amount of active carbon, and passed in turn through two columns which have been filled respectively with 200 ml. of cation exchange resin ($H^+$) (Trademark "Amberlite IR-120"; hereinafter the same) and with 400 ml. of anion exchange resin ($OH^-$) (Trademark "Amberlite IRA-68"; hereinafter the same). Effluent discharged from the second column (or refined solution) exhibits pH 6.2, and is adjusted to have 60% dried matter.

600 g. of the refined and adjusted solution as above is taken out, added 15 g. of 5%-Ru-carbon (manufactured by Nippon Engelhard Co.,Ltd.) thereto, and heated in an autoclave of 1 liter-capacity, while agitated, at a temperature of 130° C for 120 minutes under a hydrogen pressure of 150 kg./cm$^2$, to perform the hydrogenating reaction of sugars.

Hydrogenated mixture obtained is filtered to remove the catalyst, decolorized with active carbon, and further refined by passing through two columns filled with 50 ml. of cation exchange resin ($H^-$) and with 100 ml. of anion exchange resin ($OH^-$), respectively. Composition of the refined solution is estimated quantitatively by gas chromatography using an apparatus of SHIMAZU GC-4A type. Outline of the procedures is as follows:

(a) Preparation of sample: A predetermined amount of the refined solution is evaporated and dried in vacuo to remove its moisture completely, added acetic acid anhydride and pyridine thereto followed by heating the resultant mixture under reflux for an hour to convert the sugar alcohols into hexaacetate esters thereof. To this hexaacetate esters is added a predetermined amount of di-2-ethylhexyl adipate as the internal standard, to thereby prepare a sample to be injected in the gas chromatograph.

(b) Operating parameters: Column consisting of stainless steel pipe of $3m \times 3mm\phi$, which is packed with 1.5%QF-1 on Chromosorb W of 60-80 mesh; Column temp. 200° C; Detector temp. 250° C; Carrier gas flow 70 ml./min.; $H_2$ flow 50 ml./min.; Air flow 1.0 liter/min.

(c) Preparation of standard curve: Groups of samples of accurately weighed pure D-sorbitol and D-mannitol are respectively acetylated and gas chromatographed in the same manner as has been mentioned above, and thereby are prepared the standard curves illustrating the relations between peak areas on the respective gas chromatograms and the corresponding weights of the sugar alcohols used.

(d) Estimation of sugar alcohols: The sample prepared under item(a) undergoes gas chromatography with the paramaters under item(b), and respective peak areas on a gas chromatogram are measured, followed by comparing these values of areas with those on the standard curves prepared under item(c), thereby are determined the quantities of D-sorbitol and D-mannitol in the sample.

As the result of the above, it is revealed that the formation ratio of D-mannitol in the hydrogenated mixture is 31.2% based on the initial D-glucose while that of D-sorbitol is 68.8%.

The above refined solution of the hydrogenated mixture is concentrated in vacuo to a syrup, which is then cooled to crystallize out D-mannitol, the melting point of the crystals being 166.2° C. The yield is 88.6 g., corresponding to 24.6% based on the initial D-glucose.

EXAMPLE 2

An aqueous solution of crystalline D-glucose is prepared in the same way as in Example 1. To this solution is added 4.5 g. (0.15% relative to the D-glucose) of ammonium molybdate, and the resulting solution is adjusted to pH 3.5 with a dilute sulfuric acid followed by heating it in an autoclave of 10 liter-capacity, while agitated, at a temperature of 120° C for 30 minutes. Epimerized mixture obtained exhibits pH 3.2 and is light yellow in color.

500 g. of the epimerized mixture is taken out, and undergoes the refining treatment in the similar manner to that applied to the epimerized mixture in Example 1. Refined solution obtained is subjected to the catalytic hydrogenation in the similar manner to that described hereinafter in this Example, and D-mannitol formed therein is estimated quantitatively in the same way as in Example 1. As the result, it is revealed that the formation ratio of D-mannitol in the hydrogenated mixture is 31.8% based on the initial D-glucose, said value being able to be regarded as showing on the other hand the formation ratio of D-mannose in the epimerized mixture.

The remainder of the epimerized mixture is adjusted to pH 7.0 with a dilute sodium hydroxide solution, added thereto 30 g. of an enzyme preparation with Trademark "Glucose-Isomerase Nagase" (manufactured by Nagase & Co.,Ltd.; with enzyme activity of 1,000 GIU/g.), and warmed, while agitated gently and maintained at pH 6.5–7.0 during the reaction, at a temperature of 70° C for 50 hours, to perform the enzymatic isomerizing reaction of the D-glucose remaining in the epimerized mixture.

Isomerized mixture obtained is filtered to separate the enzyme, decolorized with active carbon, and passed through two columns filled respectively with 200 ml. of cation exchange resin ($H^+$) and with 400 ml. of anion exchange resin ($OH^-$). Refined solution obtained exhibits pH 6.2 and is adjusted to have 60% dried matter.

550 g. of the refined and adjusted solution as above is taken out, added 20 g. of Raney nickel thereto, and the resulting mixture is heated in an autoclave of 1 liter-capacity, while agitated, at a temperature of 120° C for 120 minutes under a hydrogen pressure of 150 kg./cm$^2$.

Hydrogenated mixture obtained is, in the same manner as in Example 1, filtered and refined followed by the quantitative estimation of sugar alcohols by gas chromatography, and thereby it is revealed that the formation ratio of D-mannitol based on the initial D-glucose is 46.4% while that of D-sorbitol is 53.6%. The above refined solution is concentrated in vacuo to crystallize out D-mannitol, the melting point of the crystals being 166.0° C. The yield is 133.0 g., corresponding to 40.3% on the initial D-glucose.

On the other hand, the formation ratio of D-fructose in the enzymatic isomerized mixture is counted backward as 29.2%, from the values of 46.4% of D-mannitol formation ratio in the hydrogenated mixture and 31.8% of D-mannose formation ratio in the epimerized mixture.

EXAMPLE 3

3.8 kg. of crystalline D-glucose on the market is dissolved in 1.2 kg. of deionized water. The resultant solution is added 3.5 g. (0.10% relative to the D-glucose) of sodium molybdate $Na_2MoO_7 \cdot 2H_2O$ thereto, adjusted to pH 3.5 with a dilute sulfuric acid, and heated in an autoclave of 10 liter-capacity, while agitated, at a temperature of 130° C for 15 minutes. Epimerized mixture exhibits pH 3.2 and is light yellow in color.

The said mixture is adjusted to pH 7.0, added 35 g. of "Glucose-Isomerase Nagase" thereto, and warmed, while agitated gently and maintained at pH 6.5–7.0 during the reaction, at a temperature of 65° C for 64 hours. Isomerized mixture obtained undergoes the refining treatment in the similar manner to that applied to the isomerized mixture in Example 2. Refined solution exhibits pH 6.2 and is adjusted to have 60% dried matter.

600 g. of the refined and adjusted solution is taken out, added 20 g. of Raney nickel thereto, and heated, while agitated, in an autoclave of 1 liter-capacity at a temperature of 130° C for 120 minutes under a hydrogen pressure of 150 kg./cm$^2$. Hydrogenated mixture is, in the same way as in Example 1, filtered and refined followed by the quantitative estimation of sugar alcohols, thereby it is revealed that D-mannitol formation ratio based on the initial D-glucose is 47.5%. The refined solution is concentrated in vacuo to crystallize out D-mannitol, the melting point of the crystals being 165.8° C. The yield is 147.6 g., which corresponds to 41.0% on the initial D-glucose.

EXAMPLE 4

Aqueous solution of crystalline D-glucose which is prepared in the same way as in Example 1 is added 3.0g. (0.10% relative to the D-glucose) of ammonium molybdate thereto, and adjusted to pH 3.2 with a dilute sulfuric acid. The resulting solution is pumped continuously with a plunger pump, at a rate of 20 ml./min., into a stainless steel reaction pipe of 0.8 cm. internal diameter and 3m. length (i.e. 150ml.-capacity) provided with a pressure gauge as well as a discharge valve, and heated, while the solution flows through the pipe, at a temperature of 140° C under a pressure of 3.0 kg./cm$^2$, to thereby perform the continuous epimerization reaction of D-glucose. Retaining time of the material solution in the pipe is about 7.5 minutes. Finished solution (or epimerized mixture) is discharged continuously from the discharge valve, which exhibits pH 2.9 and is slightly colored. The epimerized mixture is adjusted to pH 6.0 with a dilute sodium hydroxide solution and to have 60% dried matter.

550 g. of the mixture adjusted as above is taken out and subjected to the catalytic hydrogenation in the similar manner to that to the refined isomerized mixture in Example 3. The hydrogenated mixture obtained is refined, followed by the quantitative estimation of D-mannitol, and thereby it is revealed that the formation ratio of D-mannitol amounts to 33.4% based on the initial D-glucose. The refined solution is concentrated in vacuo to crystallize out D-mannitol, the melting point of the crystals being 165.8° C. The yield is 87.5 g., which corresponds to 26.5% on the initial D-glucose.

EXAMPLE 5

Aqueous D-glucose solution prepared in the same way as in Example 1 is added 1.5 g. (0.05% relative to D-glucose) of ammonium molybdate thereto and adjusted to pH 3.5 with dilute sulfuric acid. The resulting solution undergoes the continuous epimerization reaction of D-glucose, by employing the same apparatus as in Example 4, while adopting reaction conditions of a temperature of 160° C, solution pumping rate of 35 ml./min., retaining time of the solution of about 4.3 minutes and a pressure in the reaction pipe of 6.2 kg./cm$^2$. Epimerized mixture discharged continuously from the reaction pipe exhibits pH 3.1 and is slightly brown in color. This mixture is adjusted to pH 6.0 and to have 60% dried matter.

550 g. of the mixture adjusted as above is taken out and subjected to the catalytic hydrogenation in the similar manner to that to the refined isomerized mixture in Example 3, but using 30 g. of Raney nickel. Hydrogenated mixture is refined, followed by the estimation of its D-mannitol formation ratio, thereby it is revealed such ratio amounts to 35.4% based on the initial D-glucose. The refined solution is concentrated in vacuo to crystallize out D-mannitol, the melting point of the crystals being 165.6° C. The yield is 93.1 g., corresponding to 28.2% based on the D-glucose.

EXAMPLE 6

4.12 kg. of crystalline D-glucose on the market is dissolved in 0.88 kg. of deionized water. The solution is added 3.8 g. (0.10% relative to the D-glucose) of ammonium molybdate thereto and adjusted to pH 3.2 with dilute sulfuric acid. The resulting solution undergoes the continuous epimerization reaction with the same apparatus and manner as in Example 4. Epimerized mixture discharged exhibits pH 2.9 and is slightly brown in color. This mixture is adjusted to pH 6.2 and to have 60% dried matter.

550 g. of the mixture adjusted is taken out and subjected to the catalytic hydrogenation in the similar manner to that to the refined isomerized mixture in Example 3, but employing reaction period of 150 minutes. Hydrogenated mixture obtained is refined, followed by the estimation of its D-mannitol formation ratio, and thereby it is revealed such ratio amounts to 33.0% based on the initial D-glucose. This refined solution is concentrated in vacuo to crystallize out D-mannitol, the melting point of the crystals being 165.7° C. The yield is 85.2 g., which corresponds to 25.8% based on the initial D-glucose.

EXAMPLE 7

5.0 kg. of starch hydrolyzate (DE 97; 40% water content) is added 6.0g. (0.20% relative to the dried matter of the starch hydrolyzate) of sodium molybdate thereto, adjusted to pH 3.2 and heated, while agitated, in an autoclave of 10 liter-capacity at a temperature of 120° C for 35 minutes. Epimerized mixture exhibits pH 2.9 and is slightly brown in color.

500 g. of the mixture is taken out, and submitted to the determination of D-mannose formation ratio, applying correspondingly the determinating manner of D-mannose formation ratio in the epimerized mixture in Example 2, thereby it is revealed such ratio is 29.8% based on the dried matter of the starch hydrolyzate used.

The remainder of the epimerized mixture is adjusted to pH 6.6, added 50 g. of "Glucose-Isomerase Nagase" thereto, and warmed at a temperature of 70° C for 48 hours, while agitated gently and maintained at pH 6.5–7.0 during the reaction. Isomerized mixture obtained undergoes the refining treatment in the similar manner to that to the isomerized mixture in Example 2. Refined solution exhibits pH 6.2 and is made to have 60% dried matter.

600 g. of the refined and adjusted solution is subjected to the catalytic hydrogenation in the similar manner to that to the refined isomerized mixture in Example 3. After refining, the hydrogenated mixture reveals that the D-mannitol formation ratio is 42.7% based on the dried matter of the starch hydrolyzate used. This refined solution is concentrated in vacuo to crystallize out D-mannitol, the melting point of the crystals being 166.2° C. The yield is 124.0 g., which corresponds to 34.4% based on the dried matter of the starting material.

On the other hand, the D-fructose formation ratio in the enzymatic isomerized mixture is counted backward as 25.8% based on the dried matter of the starting material, from the values of 42.7% of D-mannitol formation ratio in the hydrogenated mixture and 29.8% of D-mannose formation ratio in the epimerized mixture.

EXAMPLE 8

5.0 kg. of starch hydrolyzate having the same composition as in Example 7 is added 6.0g. (0.20% relative to the dried matter of the starch hydrolyzate) of ammonium molybdate thereto, adjusted to pH 3.0, and heated, while agitated, in an autoclave of 10 liter-capacity at a temperature of 140° C for 10 minutes. Epimerized mixture exhibits pH 2.7 and is slightly brown in color. The mixture undergoes the refining treatment in the similar manner to that to the epimerized mixture in Example 1. Refined solution exhibiting pH 6.2 is adjusted to have 60% dried matter.

600 g. of the refined and adjusted solution is subjected to the catalytic hydrogenation in the similer manner to that to the refined isomerized mixture in Example 3, but using 20 g. of 2.5%Ru2.5%Rh-carbon as hydrogenating catalyst. Dried matter composition of the hydrogenated mixture obtained is 31.6% mannitol, 67.9% sorbitol and 0.5% impurities. Refined solution of the mixture is concentrated in vacuo to crystallize out D-mannitol, the melting point of the crystals being 166.1° C. The yield is 86.2 g., corresponding to 23.9% based on the dried matter of the starting material.

EXAMPLE 9

5.0 kg. of hydrol (DE 91; 40% water content) is added 6.0 g. (0.20% relative to the dried matter of the hydrol) of ammonium molybdate thereto, adjusted to pH 3.0 and heated, while agitated, in an autoclave of 10 liter-capacity at a temperature of 140° C for 10 minutes. Epimerized mixture exhibits pH 2.7 and is slightly brown in color.

500 g. of the mixture is taken out, and submitted to the determination of D-mannose formation ratio, applying correspondingly the determinating manner of D-mannose formation ratio in the epimerized mixture in Example 2, thereby it is revealed such ratio is 27.2% based on the dried matter of the hydrol used.

The remainder of the epimerized mixture is adjusted to pH 6.8, added 50 g. of "Glucose-Isomerase Nagase" thereto, and warmed at a temperature of 65° C for 48 hours, while agitated gently and maintained at pH 6.5–7.0 during the reaction. The isomerized mixture undergoes the refining treatment in the similar manner to that to the isomerized mixture in Example 2. Refined solution exhibits pH 6.2 and is adjusted to have 60% dried matter.

600 g. of the refined and adjusted solution is taken out, added 30 g. of Raney nickel thereto, adjusted to pH 3.0 with a dilute sulfuric acid, and heated, while agitated, in an autoclave of 1 liter-capacity at a temperature of 175° C for 120 minutes under a hydrogen pressure of 150 kg./cm$^2$. Hydrogenated mixture is refined, followed by the estimation of D-mannitol formation ratio thereof, and thereby it is revealed such ratio is 39.1%. The refined solution is concentrated in vacuo to crystallize out D-mannitol, the melting point of the crystals being 165.5° C. The yield is 108.6 g., which corresponds to 30.2% based on the dried matter of the starting material.

On the other hand, from the values of 39.1% of D-mannitol formation ratio in the hydrogenated mixture and 27.2% of D-mannose formation ratio in the epimerized mixture, the D-fructose formation ratio in the isomerized mixture is counted backward as 23.8% based on the dried matter of the hydrol used.

EXAMPLE 10

5.0 kg. of hydrol having the same composition as in Example 9 is added 6.0g. (0.20% relative to the dried matter of the hydrol) of molybdenum trioxide MoO$_3$ thereto, adjusted to pH 2.5 with a dilute hydrochloric acid, and heated, while agitated, in an autoclave of 10 liter-capacity at a temperature of 130° C for 20 minutes. Epimerized mixture exhibits pH 2.1 and is slightly brown in color. The mixture is adjusted to have 60% dried matter, while its pH is not adjusted.

600 g. of the mixture adjusted is taken out, added 100 g. of a catalyst with trademark "Stabilized Nickel Catalyst G-49B" (manufactured by Nissan Girdler Catalyst Manufacturing Co.,Ltd.) thereto, and heated, while agitated, in an autoclave of 1 liter-capacity at a temperature of 180° C for 120 minutes under a hydrogen pressure of 150 kg./cm$^2$. Dried matter composition of the hydrogenated mixture is 26.7% mannitol, 71.3% sorbitol and 2.0% impurities. Refined solution of the hydrogenated mixture is concentrated in vacuo to crystallize out D-mannitol, the melting point of the crystals being 165.7° C. The yield is 65.3 g. corresponding to 18.1% based on the dried matter of the hydrol used.

What we claim is:

1. Process for preparing D-mannitol which comprises:
   (A) heating a D-glucose aqueous solution at a temperature of 110°–160° C with pH 2.0°–4.5 in the presence of molybdic acid compound to convert (or epimerize) a portion of D-glucose into D-mannose,
   (B) maintaining the epimerized mixture formed at step (A) at a temperature of 65°–75° C in the presence of glucose-isomerase to convert (or isomerize) a portion of D-glucose remaining in the epimerized mixture into D-fructose,
   (C) heating the isomerized mixture formed at step (B) in the presence of a hydrogenating catalyst under high hydrogen pressure to perform the catalytic hydrogenation of sugars contained therein, and
   (D) concentrating the finished solution of step (C) to crystallize out D-mannitol.

2. Process as claimed in claim 1, wherein the dried matter concentration of the D-glucose aqueous solution is 40–80%.

3. Process as claimed in claim 1, wherein the amount of molybdic acid compound used is 0.05–0.20% based on the dried matter of the D-glucose aqueous solution.

4. Process as claimed in claim 1, wherein the reaction period of step (A) is less than 40 minutes.

5. Process as claimed in claim 1, wherein the molybdic acid compound is at least one member selected from the group consisting of ammonium molybdate, sodium molybdate, potassium molybdate, molybdenum trioxide and molybdic acid.

6. Process as claimed in claim 1, wherein the material of the D-glucose aqueous solution is one member selected from the group consisting of crystalline D-glucose, starch hydrolyzate and hydrol, both of said starch hydrolyzate and hydrol having DE above 80.

7. Process as claimed in claim 3, wherein the epimerized mixture undergoes the subsequent step (B) without any refining treatment of it but pH adjustment.

8. Process as claimed in claim 1, wherein step (B) is conducted for 48–72 hours with pH 6.5–8.5.

9. Process as claimed in claim 1, wherein step (B) is effected by using the epimerized mixture the dried matter concentration of which is 50–65%.

10. Process as claimed in claim 1, wherein step (B) is effected by applying the so-called immobilized enzyme system thereto.

11. Process as claimed in claim 1, wherein the material of the D-glucose aqueous solution is starch hydrolyzate or hydrol and step (C) is conducted under conditions of pH 2.0–3.0 and a temperature of 160°–180° C.

* * * * *